United States Patent [19]

Ho et al.

[11] Patent Number: 5,055,626

[45] Date of Patent: Oct. 8, 1991

[54] NOVEL LUBRICANTS

[75] Inventors: Suzzy C. Ho, Plainsboro; Margaret M. Wu, Belle Mead, both of N.J.

[73] Assignee: Mobil Oil Corporation, Fairfax, Va.

[21] Appl. No.: 471,454

[22] Filed: Jan. 29, 1990

[51] Int. Cl.$^5$ .................. C07C 15/00; C07C 2/52
[52] U.S. Cl. .................. 585/416; 585/420
[58] Field of Search .................. 585/416, 420

[56] References Cited

U.S. PATENT DOCUMENTS

| | | | |
|---|---|---|---|
| 2,217,011 | 10/1940 | Grosse et al. | 585/420 |
| 2,781,408 | 2/1957 | Witt et al. | 585/416 |
| 2,819,325 | 1/1958 | Lanning et al. | 585/416 |
| 4,827,064 | 5/1989 | Wu | 585/10 |
| 4,827,073 | 5/1989 | Wu | 585/530 |

OTHER PUBLICATIONS

Eapen et al., "Poly-normal-alkylbenzene Compounds: A Class of Thermally Stable and Wide Liquid Range Fluids", Preprints of Division of Petroleum Chemistry, No. 4; pp. 1053-1058, American Chemical Society, Aug. 26-31, 1984.

*Primary Examiner*—Curtis R. Davis
*Attorney, Agent, or Firm*—Alexander J. McKillop; Charles J. Speciale; Malcolm D. Keen

[57] ABSTRACT

Alkylaromatic lubricant products are produced by the reaction of a long chain alkyne such as octyne, decyne or dodecyne over a reduced Group VIB metal oxide catalyst, preferably reduced chromium on silica. The products, which are predominantly n-alkyl substituted, possess excellent thermal and oxidative stability and may be used as lubricant base stocks and viscosity improvers.

21 Claims, No Drawings

NOVEL LUBRICANTS

This invention relates to novel synthetic lubricants. It more particularly refers to synthetic alkyl aromatic lubricants and a novel process for producing them.

BACKGROUND OF THE INVENTION

In recent years there has been a pronounced effort to produce superior lubricants. Attempts to make such superior lubricant materials have revolved around improved refining of natural mineral oil base stocks and the creation of new synthetic base stocks which have good basic lubricity characteristics. Where new compounds were synthesized, there were attempts made to produce compounds which had known oxidation resistant sites, such as quaternary carbon atoms. Additionally, it was attempted to produce long chain hydrocarbon compounds, since it was known from mineral oil technology, that long chain hydrocarbons had both good lubricity and good smoke points. Although long chain aliphatic groups have good lubricating properties, they usually also have relatively high freeze and cloud points.

Thus, many synthetic lubricants are based on decene oligomers because these compounds have an excellent combination of properties including long aliphatic chains, which provide good slipperiness, relatively low freeze and cloud points, and oxidation resistant loci in the same molecules.

Recently, it has been found, by one of the inventors of the subject matter hereof, that decenes which have been oligomerized over Group VI B metal catalysts, particularly reduced chromium catalysts, produce unusually fine lubricant base stocks. The products of this oligomerization tend to have very uniform molecular structure, low branch ratios and low pour points. Fine synthetic lubricants and viscosity index (V I) improvers have been formulated from these decene oligomers, which are principally trimers. Reference is here made to U.S. Pat. Nos. 4,827,064 and 4,827,073, issued in the name of one of the inventors hereof, which show the novel production of excellent alpha olefin oligomers which find utility in the lubricant field.

Alkyl aromatics are very well known organic compounds. They have a wide variety of known uses in detergent and lubricant technologies, and they have been used as precursors for producing over-based aryl sulfonates.

In general, alkyl aromatics have usually been made by alkylating existing, preformed aromatic compounds, such as benzene, toluene, xylene, naphthalene, etc., with alpha olefins. There has recently arisen an interest in finding alkyl aromatics which would be useful in lubricant formulations. Inherently, these materials should make good lubricant base stocks because they have long alkyl chains to provide the needed lubricity characteristics, and aromatic nuclei which should provide good oxidation resistance and solvency for polar additives, such as antiwear additives, antioxidants, etc. Further, their molecular structure is such that these molecules should have relatively low freeze and cloud points.

Alkyl aromatics are commercially available materials. They are conventionally synthesized by the direct addition of olefins, particularly alpha olefins, to aromatic nuclei, particularly benzene. This reaction is known to produce a mixture of mono and multi substituted benzenes in which the alkyl groups may be straight or branched chain. Indeed, some of the alkyl substituents may be straight chain and others may be branched chain in the same molecule.

Reference is here made to an article by K. C. Eapen et al. *Poly-normal-alkylbenzene Compounds: A Class of Thermally Stable and Wide Liquid Range Fluids*: Preprints of the Division of Petroleum Chemistry, No. 4, pages 1053-1058 American Chemical Society, Philadelphia Meeting, Aug. 26-31, 1984. This article reviews the state of the art relative to making alkyl aromatic compounds for use as lubricants, as well as a review of the properties of such lubricants as have been made with these base stocks. It is well known, from conventional inorganic chemistry, that reactions requiring stoichiometric quantities of Grignard reagents as described in this reference, are difficult and expensive to run. Further, it is known that this type of reaction is difficult to control in that the amount of alkylation and the particular position of the alkyl substitution may not always be exactly where it is most desired that it be. As a result, while the reaction may be generally known, the production of reaction products which are suited to use as lubricants is in no way shown by this reference, nor is it possible to use this stoichiometric Grignard reagent reaction to produce lubricant quality products.

In this art, it is to be noted that the lubricant base stock is often the whole reaction product, or at least a substantial portion thereof, with a minimum of product purification. It is most unusual for a pure compound or compounds to be used as a lubricant base stock because the cost of isolation of a pure compound would be so significant that the product so produced might well be priced out of the market almost regardless of the properties that it possessed. Thus, the lubricant base stock which is actually used is usually a mixed reaction product which has been refined to the least extent possible consistent with obtaining the properties which are desired.

SUMMARY OF THE INVENTION

Thus, this invention is directed to a novel process for producing lubricant base stocks which are predominantly n-alkyl aromatic in nature, have high viscosity index, low pour point, good thermal oxidation stability, and good additive solubility. This process comprises the reaction of a substituted acetylene, a 1-alkyne, in contact with a transition metal catalyst, preferably activated metal on a refractory substrate, under conditions conducive to the aromatization of the 1-alkyne, into alkyl substituted aromatic compounds, in which the alkyl portions are derived from the alkyl portions of the substituted acetylene, and the cyclic, aromatic portions are derived from the cyclooligomerization of the alkyne portion of the reactant molecules (the cyclization and aligomerization the reactant). One particularly desirable attribute of the process of this invention is the fact that the catalysts are regenerable and reusable, and do not leave the reaction zone as a necessary adjunct to the reaction product requiring later separation and purification.

DETAILED DESCRIPTION OF THE INVENTION

According to one aspect of this invention, a desired product mixture comprising alkyl aromatics is produced by contacting substituted acetylenes with a suitable catalyst under aromatization conditions. The nature of the product mixture is very much a function of the substituted acetylene, or 1-alkyne, which is used as the reactant.

According to this invention, the 1-alkyne reactant used herein suitably contains between about 8 and 20 carbon atoms which are preferably in a substantially straight chain configuration. Although straight chain reactant alkynes are preferred, it is within the scope of this invention to utilize alkyne reactants which have some branching in the molecule.

The existence of branching has little or no effect upon the conversion of the alkyne to the desired alkyl aromatic, unless the branching is so close to the alkyne group that it offers spatial interference with the aromatization reaction. Thus, it is preferred that, if the reactant alkyne contains branches these branches be somewhat distant from the alkyne group so as to pose minimum spatial interference with the aromatization of the alkyne group portion of the reactant molecule. On the other hand, straight chain aliphatic molecule portions seem to have the best lubrication properties, and so branch chains, if any, should not be far away from the aromatic group in the product molecule because then such branches might interfere with the desired lubricating properties of the product. It is preferred to have relatively long branch chains. These long dependant groups do not substantially adversely affect the VI of the lubricant product and substantially improve the pour point thereof.

Substituted acetylenes which are suited to use in this invention are preferably about eight (8) to eighteen (18) carbon atoms long with up to about two (2) lower alkyl branches. Illustrative 1-alkynes include: octyne, decyne, dodecyne, 4-methyldodecyne, eicosyne, mixtures of various long chain 1-alkynes, etc. These starting reactants are generally available in the open market.

The catalyst which is used in this invention is generally a transition metal supported on a porous substrate. The transition metal is preferably a Group VI B metal, and is most preferably chromium. The substrate may be any porous, refractory material. It is preferred, however, that the substrate be a material which is substantially inert with respect to the reactants and the products produced in the process hereof. Silica is the most preferred catalyst substrate. According to this invention, the Group VI B metal should be in a reduced state.

It is important to the practice of this invention that the aromatization conditions be such as not to isomerize the alkyne bond from a terminal position to an interior position prior to or during the aromatization reaction. If the triple bond isomerizes to an internal position and then is aromatized from that position, the number of alkyl groups on the product aromatic nucleus will increase, and the chain length of each will correspondingly decrease, thus adversely affecting the lubricating properties of the product. Internal triple bonds thus created by unintentional isomerization have substantially lower reactivity and are therefore detrimental to the overall yield achieved by this process. It is also very important that the triple bond of the reactant 1-alkyne not be isomerized into a conjugated, or non-conjugated pair of double bonds as a result of the process conditions hereof because then the reactant molecule would not be capable of being directly aromatized as is required by the practice of this invention.

Thus, the selection of the operating conditions, and of the particular catalyst in combination with these operating conditions, is of great importance in the practice of this invention. Excellent properties, with respect to catalyzing the desired aromatization reaction, without significant catalysts of the undesired isomerization reactions, are possessed by Cr II on high surface area silica. Good conversion can also be achieved by the use of reduced tungsten and/or molybdenum based catalysts. In addition to the silica support, alumina, titania, silica alumina, magnesia and the like have been found to be useful as support materials either singly or in various combinations.

The support material, regardless of its composition, should have high surface area, suitably provided by a pore system of average pore size of about 40 to 350 (Å) angstroms. The high surface area is beneficial in supporting large amounts of highly dispersed, active Group VI B metal centers so as to give high efficiency of metal catalyst usage. This results in high catalyst activity for the specific reaction desired without undesirable catalysis of isomerization reactions. The substrate should preferably have average pore openings of about 60 to 300 (Å) angstroms, such that the pores will not impose undue diffusional limitations on the reactants reaching the reactive catalytic cites. More importantly, large pores permit and encourage the more bulky products to readily diffuse away from the catalytic cites thereby leaving them open for further use.

The process of this invention can be carried out in a fixed bed, a fixed fluidized (ebulating) bed or a transport type fluidized bed, as desired. Slurry bed reaction zones are also suitable. The support used must have sufficient physical strength, and be sufficiently tightly bound to the metal catalyst, that its use in the rugged environment of a fluidized bed will not adversely affect it physically or chemically.

One suitable method of preparing the supported reduced transition metal catalysts of this invention is by impregnating a suitable metal salt or salts, dissolved or suspended in a suitable organic carrier or water, into the substrate. Suitable organic carriers include: methanol, ethanol, acetic acid and the like. After impregnation and suitable drying, the solid catalyst precursor is calcined at about 200° to 900° C. in an oxidizing atmosphere, suitably air, or air enriched in oxygen, or even oxygen itself. Thereafter, the catalyst is reduced by contact thereof with a suitable reducing agent such as: carbon monoxide; hydrogen; ammonia; hydrogen sulfide; carbon disulfide; dimethyl sulfide; dimethyl disulfide; or organometallic compounds such as alkyls, alkoxyls or aryls of aluminum, boron, magnesium, lithium, or zinc. It is preferred to reduce the metal catalyst with carbon monoxide, hydrogen or a metal alkyl organometallic. The amount of active metal catalyst is suitably about 0.1 % to 20 % by weight on the basis of the entire catalyst. The weight ratio of the alkyne reactant to the catalyst suitable ranges from about 1 to 1 to 10,000 to 1.

Another suitable method of preparing the metal catalysts of this invention is to pre-reduce the metal, for example in the case of chromium to the II state, and then apply the reduced metal to the substrate. In this preparation, it is important to exclude contact with substantial proportions of oxygen, or other oxidizing agents, during the preparation of the catalyst.

A different, but substantially equally as effective catalyst preparative technique, adds the selected support material to a solution, emulsion or slurry of suitable metal compounds, such as acetates or nitrates. The mixture is dewatered (or has the organic solvent removed), suitably at room temperature, but perhaps at slightly elevated temperatures, to produce a gel which is then subjected to successively elevated temperatures up to about 600° C. over a period of about 16 to 20 hours. Thereafter, the supported catalyst is cooled down, under an inert atmosphere, to about 250° to 450° C. and a stream of suitable reducing medium, preferably carbon monoxide, is contacted therewith until a distinct color change appears, in the case of chromium from bright orange to pale blue. It is common for the reducing agent to be used in a proportion relative to the supported metal, of about twice. After this treatment, the supported, reduced catalyst is cooled to room temperature and then used directly or stored for future use.

The catalysts prepared as set forth above, or by other means to produce similarly reduced Group VI B metals, are very active for this aromatization reaction. The aromatization reaction is suitably carried out at about $-30°$ to 250° C., preferably about room temperature to 180° C., at autogenous pressure, suitably about 0.1 to 5000 psi. Reaction contact times do not appear to be critical and can vary from about 1 second to 24 hours. It is preferred, for best results, however, to carry out this reaction at a weight hourly space velocity (WHSV) of about 0.1 to 10, based on the total catalyst (with support) weight. As previously noted, the catalyst may be used in a fixed or a fluid or a slurry bed, as desired. Its particle size will vary depending upon the type of reaction zone that is chosen.

The trimer product usually predominates in two (2) products, the 1, 2, 4 and the 1, 3, 5 trialkyl benzenes. The product ratios of these are about 85/15 to 30/70 respectively, depending upon the reaction conditions, such as the reaction temperature, the activated metal, particularly chromium, loading, and the weight ratio of the alkyne reactant to the catalyst. Within this range of isomers proportions, there is little or no effect on the lubricant properties of the product. Generally, the products have high VI's of at least about 95, and low pour points, as well as viscosities of at least about 2.5 cs.

The practice of this invention will be illustrated by the following examples in which all parts and percentages are by weight unless expressly stated to be on some other basis.

EXAMPLE 1

Catalyst Preparation and Activation 1.9 grams (5.58 moles) of chromium II acetate is dissolved in 50 ml of hot acetic acid. 50 grams of silica gel (8-12 mesh; surface area of 300 m²/gm; and 1 ml/gm pore volume) is added to the solution whereupon most of the liquid is absorbed by the silica gel. The thus obtained mixture is further mixed for about ½ hour under vacuum at room temperature and thus dried. Then the dry material is purged under nitrogen at 250° C. in a tube furnace; the furnace temperature is raised to 400° C. for about 2 hours; then the temperature is raised to about 600° C. under dry air for about 16 hours; and finally, the catalyst is cooled down by contact with a stream of nitrogen to about 300° C. The thus made catalyst is then contacted with a stream of substantially pure carbon monoxide for about 1 hour, after which the reduced catalyst is cooled to room temperature under a nitrogen blanket.

EXAMPLE 2

Catalyst Preparation and Activation

A commercially available catalyst, having a large pore volume, a high surface area, and containing 1 % chromium on silica gel was purchased from the PQ Corporation (C2303). This material was calcined in air at 700° C. for 16 hours and then reduced with carbon monoxide at 350° C. for 1 hour whereupon the reduced catalyst was cooled to room temperature under a nitrogen blanket and thereafter kept free from contact with oxidants.

EXAMPLE 3

25 Parts of 1-decyne were mixed with 3 parts of the activated chromium catalyst prepared in Example 2. The reaction mixture was stirred at room temperature overnight, whereupon the organic liquid was separated by centrifuge. The reaction product was analyzed to contain 16% unreacted 1-decyne; 3% other C-10 compounds; and 81% of C-30 compounds. The C-30 component comprised about 75% 1, 2, 4-tri-n-octyl benzene and about 25% 1, 3, 5 tri-n-octyl benzene. These were determined by a combination of infrared analysis, gas chromatographic analysis, and C-13 NMR analysis. The C-30 product had the following properties:

V@100° C.: 3.88 cS
V@40° C.: 16.5 cS
VI: 131
Pour Point: $-80°$ C.

EXAMPLE 4

Example 3 was repeated with the exception that the reactant was 1-dodecyne, and the principal product isomers were 1, 2, 4-tri-n-decyl benzene and 1, 3, 5 tri-n-decyl benzene. The product composition had the following properties:

V@100° C.: 5.35 cS
V@40° C.: 25.1 cS
V I: 155
Pour Point: 2° C.

EXAMPLE 5

Example 3 was repeated except that 1-octyne was substituted for the 1-decyne. The principal isomers of the product were 1, 2, 4 tri-n-hexyl benzene and 1, 3, 5 tri-n-hexyl benzene. The product had the following properties:

V@100° C.: 2.6 cS
V@40° C.: 9.8 cS
V I: 99

What is claimed is:

1. A process for producing a lubricant base stock composition comprising contacting a long chain 1-alkyne comprising an alkyne portion and an alkyl portion with a solid refractory catalyst comprising a reduced Group VI B metal under aromatization conditions sufficient to effect cyclization and oligomerization of said alkyne, and recovering from the reaction a product comprising a major proportion of a multiple long chain alkyl substituted benzene, the alkyl portions of which correspond substantially to said alkyl portions of said 1-alkyne, having lubricant base stock properties.

2. A process as claimed in claim 1 wherein said 1-alkyne comprises a hydrocarbon compound containing about 8 to 22 carbon atoms.

3. A process as claimed in claim 2 wherein said 1-alkyne comprises at least one compound having about 10 to 18 carbon atoms.

4. A process as claimed in claim 1 wherein said 1-alkyne comprises at least one of octyne, decyne and dodecyne.

5. A process as claimed in claim 1 wherein said metal is selected from chromium, tungsten and molybdenum.

6. A process as claimed in claim 1 where said metal is chromium.

7. A process as claimed in claim 1 wherein said metal has been reduced by contact with carbon monoxide.

8. The process as claimed in claim 1 including carrying out said aromatization at about $-30°$ to $250°$ C.

9. The process as claimed in claim 1 including carrying out said aromatization at about room temperature to about $180°$ C.

10. The process as claimed in claim 1 including carrying out said aromatization at about 0.1 to 5000 psi pressure.

11. The process as claimed in claim 1 including carrying out said aromatization at a space velocity of about 0.1 to 10 WHSV.

12. The process as claimed in claim 1 wherein said metal is supported on a porous refractory substrate.

13. A process for producing a substituted aromatic composition, which comprises aromatizing a 1-alkyne comprising an alkyne portion and an alkyl portion with a solid catalyst comprising a reduced chromium oxide catalyst under aromatization conditions at a temperature up to about $250°$ C. to effect cyclization and oligomerization of the 1-alkyne to form an alkyl substituted aromatic in which the alkyl substituents are derived from the alkyl portions of the 1-alkyne.

14. A process as claimed in claim 13 wherein said 1-alkyne comprises at least one compound having about 10 to 18 carbon atoms.

15. A process as claimed in claim 14 wherein said 1-alkyne comprises at least one of octyne, decyne and dodecyne.

16. A process as claimed in claim 13 wherein the reduced chromium oxide catalyst has been reduced by contact with carbon monoxide.

17. A process as claimed in claim 16 in which the reduced chromium catalyst has been produced by oxidation of a chromium compound on a silica support at a temperature of from about $200°$ to $900°$ C., followed by reduction with carbon monoxide at a temperature of from about $250°$ to $450°$ C.

18. A process for producing a substituted aromatic composition, which comprises aromatizing a 1-alkyne in the presence of a solid catalyst comprising a carbon monoxide-reduced chromium oxide catalyst under aromatization conditions to effect cyclization and oligomerization of the 1-alkyne to form an alkyl substituted aromatic.

19. A process as claimed in claim 18 which is carried out at a temperature up to about $250°$ C.

20. A process as claimed in claim 19 wherein 1-alkyne comprises at least one compound having about 10 to 18 carbon atoms.

21. A process as claimed in claim 18 in which the recuced chromium catalyst has been produced by oxidation of a chromium compound on a silica support at a temperature of from about $200°$ to $900°$ C., followed by reduction with carbon monoxide at a temperature of from about $250°$ to $450°$ C.

* * * * *